United States Patent
Miwa

(10) Patent No.: US 8,617,632 B2
(45) Date of Patent: Dec. 31, 2013

(54) COFFEE WHITENER, PROCESS FOR PRODUCING SAME, AND PROCESS FOR PRODUCING BEVERAGE

(75) Inventor: Noriko Miwa, Kanagawa (JP)

(73) Assignees: Ajinomoto Co., Inc., Tokyo (JP); Amano Enzyme Inc., Nagoya-shi (JP)

(*) Notice: Subject to any disclaimer, the term of this patent is extended or adjusted under 35 U.S.C. 154(b) by 0 days.

(21) Appl. No.: 13/601,052

(22) Filed: Aug. 31, 2012

(65) Prior Publication Data

US 2013/0236627 A1    Sep. 12, 2013

Related U.S. Application Data

(63) Continuation of application No. PCT/JP2011/054884, filed on Mar. 3, 2011.

(30) Foreign Application Priority Data

Mar. 4, 2010  (JP) ................................. 2010-048312

(51) Int. Cl.
*A23C 11/04*   (2006.01)

(52) U.S. Cl.
USPC ............. 426/594; 426/42; 426/656; 426/601; 426/602

(58) Field of Classification Search
USPC ............................ 426/594, 656, 601, 602, 42
See application file for complete search history.

(56) References Cited

U.S. PATENT DOCUMENTS

| | | | |
|---|---|---|---|
| 5,024,849 A * | 6/1991 | Rasilewicz | 426/656 |
| 6,171,640 B1 * | 1/2001 | Bringe | 426/656 |
| 6,251,651 B1 | 6/2001 | Yamaguchi et al. | |
| 6,566,134 B2 * | 5/2003 | Bringe | 435/410 |
| 7,094,751 B2 * | 8/2006 | Bringe | 514/5.5 |
| 7,279,298 B2 * | 10/2007 | Yamaguchi et al. | 435/15 |
| 7,718,602 B2 * | 5/2010 | Bringe | 514/21.2 |
| 2007/0254065 A1 | 11/2007 | Kodera et al. | |
| 2011/0151005 A1 | 6/2011 | Ylikomi et al. | |
| 2011/0151055 A1 * | 6/2011 | Miwa et al. | 426/42 |

FOREIGN PATENT DOCUMENTS

| | | |
|---|---|---|
| CA | 2043232 | * 11/1991 |
| CN | 1056800 A | 12/1991 |
| JP | 1-160458 | 6/1989 |
| JP | 2-968 | 1/1990 |
| JP | 2-257838 | 10/1990 |
| JP | 6-125706 | 5/1994 |
| JP | 6-253735 | 9/1994 |
| JP | 8-224063 A | 9/1996 |
| JP | 2000-50887 | 2/2000 |
| JP | 2001-218590 | 8/2001 |
| JP | 2003-9785 | 1/2003 |
| JP | 2003-235462 A | 8/2003 |
| JP | 2003-250460 | 9/2003 |
| WO | 2006/075772 | 7/2006 |
| WO | 2009/154212 | 12/2009 |

OTHER PUBLICATIONS

International Search Report in Application PCT/JP2011/054884 issued May 10, 2011.
Written Opinion issued in PCT/JP2011/054884 on Oct. 2, 2012.
Yamaguchi et al., Appl. Environ. Microbiol., vol. 66, No. 8, (2000) pp. 3337-3343.
Yamaguchi et al., Eur. J. Biochem., 268, (2001) pp. 1410-1421.
K. Hinz, et al., International Dairy Journal, vol. 17, (2007) pp. 289-293.
Combined Chinese Office Action and Search Report issued Mar. 26, 2013, in Chinese Patent Application No. 201180012419.3 with English translation.

* cited by examiner

*Primary Examiner* — Anthony Weier
(74) *Attorney, Agent, or Firm* — Oblon, Spivak, McClelland, Maier & Neustadt, L.L.P.

(57) ABSTRACT

Coffee whiteners prepared by using, as the aqueous phase thereof, a casein-containing milk protein solution that has been deamidated with a protein deamidating enzyme, exhibit excellent storage stability and dispersibility in coffee without the use of synthetic emulsifiers.

14 Claims, No Drawings

COFFEE WHITENER, PROCESS FOR PRODUCING SAME, AND PROCESS FOR PRODUCING BEVERAGE

CROSS REFERENCES TO RELATED APPLICATIONS

This application is a continuation of International Patent Application No. PCT/JP2011/054884, filed on Mar. 3, 2011, and claims priority to Japanese Patent Application No. 2010-048312, filed on Mar. 4, 2010, both of which are incorporated herein by reference in their entireties.

BACKGROUND OF THE INVENTION

1. Field of the Invention

The present invention relates to liquefied coffee whiteners comprising vegetable oil. In more detail, the present invention relates to coffee whiteners, which exhibit outstanding emulsification stability on storage without using a synthetic emulsifier, and in which the emulsification dispersibility at the time of adding the coffee whitener to hot drinks, such as coffee, is improved.

2. Discussion of the Background

A coffee whitener is a cream-like oil-in-water emulsion which is used for reducing a bitter taste, an astringent taste, and the like or giving a dense taste by adding it to coffee, tea, and the like. Usually, an edible oil, used as the main material, an emulsified liquid which is added with an emulsifier and, if necessary, added with a milk component, a thickener, flavor, etc. is emulsified by an emulsifying machine such as a high-pressure homogenizer superior in shear force, to thereby prepare the coffee whitener. While many coffee whiteners are kept refrigerated, it is required to be stable such that a separation (oil-off) of fatty oil and a denaturation (feathering) of milk protein due to the addition to hot coffee, tea, etc. do not occur when it is used. In order to secure the stability, usually, synthetic emulsifiers, such as glycerin fatty acid ester, propylene glycol fatty acid ester, sucrose fatty acid ester, sorbitan fatty acid ester, and poly glycerine fatty acid ester, are used so much.

However, the emulsifier has an inherent acerbity, bitter taste, etc., and there is a fault that excellent flavor, taste, and texture of a food to be used are impaired. In addition, generally, the emulsifier has poor solubility, it is necessary to agitate the emulsifier with heating at 60 to 70° C. for dissolving uniformly, and there is also a problem in the work. Furthermore, although a labeling of an "emulsifier" is needed for the food which uses an emulsifier in Japan, in recent years, it has been increased to provide a product without labeling an emulsifier because of an enhancement in consumers' healthy consciousness, so that it is desired to develop a food material which can replace the function of an emulsifier. Therefore, while there have been various attempts for replacing an emulsifier, such attempts are running positively especially in a baking field, however, there is almost no example in a coffee whitener.

So far, various things are indicated about the emulsifier which uses a protein derived from milk (milk protein) such as casein, milk whey protein, etc. as raw materials. For example, there are disclosures as follows: an emulsifier comprised of polypeptide which consists of 5 to 50 amino acids obtained from a reaction product acquired by making proteolytic enzyme act on all the caseins (see Japanese Patent Kokoku Publication No. JP2-968B); a milk protein surfactant characterized in that by making proteolytic enzyme act on milk protein, and partially hydrolyze to a degree of degradation into a range of 5 to 20% (see Japanese Patent Kokai Publication No. JP01-160458A); and an oil-in-water emulsified oil composition characterized by containing a hydrolysate which contains the milk whey protein as the main ingredients hydrolyzed with an enzyme (see Japanese Patent Kokai Publication No. JP02-257838A), etc. In addition, a method has been reported that an emulsification stability of a fat-containing food and the like is increased by combining an emulsifier and casein, for example, there are disclosures of the emulsion stabilizer for milk beverages containing a hydrophilic emulsifier, sodium caseinate and k-carageenan (see Japanese Patent Kokai Publication No. JP06-253735A); an emulsion stabilizer for milk beverages comprising sucrose fatty acid ester, glycerin fatty acid ester, sorbitan fatty acid ester, glycerin succinic acid fatty ester and sodium caseinate as essential ingredients (see Japanese Patent Kokai Publication No. JP-P06-125706A); a method, in which decomposed casein is contained, as an emulsion stabilizer (see Japanese Patent Kokai Publication No. JP-P2003-9785A) etc. However, all are combined use with a synthetic emulsifier, and there are no reports of completely substituting for the function of the synthetic emulsifier in a coffee whitener.

In the meanwhile, a protein deamidating enzyme, which acts directly on an amide group in proteins, is an enzyme which catalyzes a reaction of deamidation. Thereby it causes transformation of glutamine residue into glutamic acid residue to generate a carboxylic group, which results in an increase of negative charge, an increase of electrostatic repulsive force, a decrease of isoelectric point, an increase of hydration capability etc. of protein. As a result, it has been known that various improvements of functionalities such as an increase of solubility of protein and dispersion of protein in water, and an improvement of emulsification ability etc. are afforded (see Yamaguchi et al., Appl. Environ. Microbiol., 66, p. 3337-3343 (2000); Eur. J. Biochem 268 p. 1410-1421 (2001); Japanese Patent Kokai Publication No. JP-P2000-50887A; Japanese Patent Kokai Publication No. JP-P2001-218590A; Japanese Patent Kokai Publication No. JP-P2003-250460A; WO 2006/075772; and WO 2009/154212). In addition, a method of using the protein deamidating enzyme in food products is disclosed in Japanese Patent Kokai Publication No. JP-P2000-50887A; Japanese Patent Kokai Publication No. JP-P2003-250460A; WO 2006/075772; and WO 2009/154212. Among these prior Literatures, there is a description relating to an alteration of functional properties of wheat gluten, milk protein (mainly, whey protein) using the enzyme. It is also disclosed in Japanese Patent Kokai Publication No. JP-P2000-50887A that good dispersbility and solubility and palate were shown when the coffee whitener prepared using the deamidated gluten treated with the protein deamidating enzyme showed a stable emulsion state and it was added to coffee. However, this coffee whitener is what is manufactured using monoglyceride and polysorbate which are synthetic emulsifiers, and it is actually related to the method to improve the solubility and dispersibility of gluten, and it is definitely not suggested to manufacture a coffee whitener in which synthetic emulsifier is not used.

Moreover, the treatment with the protein deamidating enzyme is recognized to effect a change in higher-order structure of protein accompanying the increase in a negative charge of protein and an increase in surface hydrophobicity, and it leads to an increase in an emulsification ability. However, since the casein which is the main milk protein inherently has a random coil configuration with low regularity and amphiphilic structure, it is known as a protein which is more excellent in emulsification ability for many years. Therefore, there are scarcely examples which aimed at an improvement of the emulsifying function of the milk protein using this enzyme anew. It is also disclosed in Japanese Patent Kokai Publication No. JP-P2000-50887A that the deamidated casein shows high solubility under existence of high concentrated calcium. In addition, a method to use the protein deamidating enzyme for yogurt, cheese, and a pudding is disclosed in WO 2006/075772, and a method of manufacturing the starch-containing food, in which color, gloss and texture are good and the time degradation after cooking was controlled, by adding the milk which was treated with the protein deamidating enzyme to a starch-containing food such as bread and sauce is disclosed in WO 2009/154212. However, in the manufacture of the coffee whitener, any example which uses the protein deamidating enzyme has not yet reported so far as an attempt for especially substituting for a synthetic emulsifier.

Thus, there remains a need for improved coffee whiteners.

SUMMARY OF THE INVENTION

Accordingly, it is one object of the present invention to provide novel coffee whiteners.

It is another object of the present invention to provide novel coffee whiteners which exhibit good stability.

It is another object of the present invention to provide novel coffee whiteners which exhibit good dispersibility.

It is another object of the present invention to provide novel beverages which contain such a coffee whitener.

It is another object of the present invention to provide novel methods of preparing such a coffee whitener.

It is another object of the present invention to provide novel methods of preparing such a beverage.

Thus, the present invention aims to provide a coffee whitener which is excellent in not only storage stability but also dispersibility in drinks such as coffee, without using a synthetic emulsifier, a process for producing same, and a process for producing beverage using same.

These and other objects, which will become apparent during the following detailed description, have been achieved by the inventors' discovery that a coffee whitener comprising an oil-in-water emulsion in which a deamidation treatment product of a milk protein containing casein such as sodium caseinate or defatted milk powder, among various milk protein materials, and vegetable oil were mixed and homogenized exhibits excellent storage stability and dispersibility to coffee.

Thus, the present invention provides:

(1) A coffee whitener, which meets all the following conditions (a)-(f):

(a) the coffee whitener is an oil-in-water emulsion having an aqueous phase of 60-90% by weight and an oil phase of 10 to 40% by weight;

(b) the aqueous phase is a casein-containing milk protein solution in which a casein-containing milk protein content is 0.05 to 5% by weight;

(c) the milk protein has been subjected to a treatment with a protein deamidating enzyme;

(d) the deamidation has a degree of a deamidation rate of 70% or above;

(e) the oil phase is vegetable oil; and (f) no synthetic emulsifier is contained as an active ingredient.

(2) The coffee whitener according to (1), wherein its pH is 6.7 to 7.8.

(3) The coffee whitener according to (1) or (2), wherein the solution of the condition (b) is a solution containing sodium caseinate of 0.05 to 5% by weight or a solution containing defatted milk powder of 0.1 to 15% by weight.

(4) The coffee whitener according to any one of (1) to (3), wherein the protein deamidating enzyme of the condition (c) is an enzyme derived from genera *Chryseobacterium*.

(5) A method for producing a coffee whitener in which no synthetic emulsifier is used, characterized by comprising the following steps (A)-(C):

(A) a step of preparing a casein-containing milk protein solution in which a casein-containing milk protein content is 0.05 to 5% by weight;

(B) a step that a protein deamidating enzyme is added to and allowed to act on the casein-containing milk protein solution so as to prepare a deamidated milk protein solution whose deamidation rate is 70% or above; and (C) a step that an aqueous phase of 60 to 90 parts by weight comprising a deamidated milk protein solution and an oil phase of 10 to 40 parts by weight comprising vegetable oil are mixed and homogenized so as to prepare an oil-in-water emulsion.

(6) The method according to (5), wherein the solution of the step (A) is a solution containing sodium caseinate of 0.05 to 5% by weight or a solution containing defatted milk powder of 0.1 to 15% by weight.

(7) The method according to (5) or (6), wherein an addition amount of the protein deamidating enzyme of the step (B) is 0.1 to 100 units per 1 g of milk protein.

(8) The method according to any one of (5) to (7), wherein the protein deamidating enzyme of the step (B) is an enzyme derived from genera *Chryseobacterium*.

(9) A method for producing a coffee whitener, in which no synthetic emulsifier is used, characterized by comprising the following steps (D)-(F):

(D) a step that a protein deamidating enzyme is added to and allowed to act on the casein-containing milk protein so as to prepare a deamidated milk protein whose deamidation rate is 70% or above;

(E) a step of preparing a deamidated milk protein solution in which a deamidated milk protein content is 0.05 to 5% by weight; and (F) a step that an aqueous phase of 60 to 90 parts by weight comprising the deamidated milk protein solution and an oil phase of 10 to 40 parts by weight comprising vegetable oil are mixed and homogenized so as to prepare an oil-in-water emulsion.

(10) The method according to (9), wherein an addition amount of the protein deamidating enzyme of the step (D) is 0.1 to 100 units per 1 g of the milk protein.

(11) The method according to (9) or (10), wherein the protein deamidating enzyme of the step (D) is an enzyme derived from genera *Chryseobacterium*.

(12) A method for producing a beverage using the coffee whitener produced by the method according to any one of (5) to (11).

According to the present invention, a coffee whitener which is excellent in storage stability and dispersibility, without using a synthetic emulsifier can be obtained.

DETAILED DESCRIPTION OF THE PREFERRED EMBODIMENTS

Hereafter, the present invention is explained in detail. The coffee whitener containing a specific oil-in-water emulsion of the present invention is an additive to drinks, such as coffee and tea, as a substitute for milk or cream, and is usually prepared as a homogeneous composition containing a proper quantity of water, vegetable oil, and a milk constituent. As the vegetable oil used for the oil phase, ones that is usually used for food, for example, canola oil, cottonseed oil, corn oil, sunflower seed oil, soybean oil, coconut oil, palm kernel oil, palm oil, and derivatives that are hardened or fractionated therefrom are included. These are used, if necessary, in combination suitably. Notably, since there is an advantage that an oil-off (fat separation) of the coffee whitener is hardly caused, a fat which is a liquefied state at normal temperature and especially near 20 to 30° C. is used preferably.

The deamidated milk protein solution, whose deamidation rate is 70% or above and 100% or less, is obtained by deamidating the casein-containing milk protein with the protein deamidating enzyme, is used for the aqueous phase of the coffee whitener of the present invention. As raw materials of the milk protein to which enzymatic treatment is applied, casein, sodium caseinate, or casein-containing milk raw materials such as non-fat milk, defatted milk powder, whole milk powder, and milk are used. As for the quantity of the milk protein in the solution, 0.05 to 5% by weight is preferable, and 0.15 to 3% by weight is more preferable. In the case where defatted milk powder is used, as for the content of defatted milk powder in the aqueous phase, depending on the protein content in the defatted milk powder, 0.1 to 15% by weight is preferable, 0.4 to 11% by weight is more preferable, and 1.5 to 9% by weight is further more preferable, when the protein content in the defatted milk powder is 36%, for example.

The protein deamidating enzyme used for the present invention is not limited as far as it possesses a function to directly act on amide group in a protein, so as to cut a peptide bond and deamidate the protein without cross-linking. As an example of such an enzyme, a protein deamidating enzyme derived from genera *Chryseobacterium*, genera *Flavobacterium*, or genera *Empedobacter* as disclosed in JP2000-50887A, JP2001-218590A, and WO2006/075772, all of which are incorporated herein by reference in their entireties, a protein glutaminase, commercially available in the market, derived from genera *Chryseobacterium* and the like are exemplified but not limited thereto. Preferably, an enzyme derived from genera *Chryseobacterium* is used. As for transglutaminase, it is not included in a protein deamidating enzyme according to the present invention because when the transglutaminase acts on food materials, it brings about a cross-linking reaction, with priority, in proteins and almost no deamidating reaction.

As the protein deamidating enzyme, one which is prepared from a culture liquid of a microorganism that produces the protein deamidating enzyme can be used. Known separation and purification methods of protein (such as centrifuging, UF concentration, salting-out, various kinds of chromatography with ion-exchanging resin, etc.) can be used as the preparation method of a protein deamidating enzyme. For example, a culture liquid is centrifuged to separate bacteria cells, and then salting-out and chromatography, and the like may be combined to obtain the target enzyme. When collecting the enzyme from the interior of bacterial cells, bacterial cells can be crushed by a pressure processing or ultrasonic processing, for example, and then separated and purified as described above to obtain the target enzyme. Bacterial cells may be recovered from a culture liquid by filtration or centrifuge, etc. prior to the processing steps above explained (such as crushing of bacterial cells, separation and purification). The enzyme may be powdered by a drying method such as freeze drying or vacuum drying, etc., and an appropriate bulking agent or drying adjuvant may be used at the drying step.

The activity of the protein deamidating enyme in the present invention is measured by the following method:

(1) 0.1 ml of an aqueous solution containing a protein deamidating enzyme is added to 1 ml of 0.2 M phosphate buffer (pH=6.5) containing 30 mM Z-Gln-Gly (wherein Z is a benzyloxycarbonyl group, i.e., N-benzyloxycarbonyl-L-glutaminylglycine), and incubated at 37° C. for 10 minutes, and then reaction is ceased by adding 1 ml of 0.4 M TCA solution. 0.1 ml of an aqueous solution containing the protein deamidating enzyme is added to a solution containing 1 ml of 0.2M phosphate buffer (pH=6.5) containing 30 mM Z-Gln-Gly and 1 ml of 0.4 M TCA solution, and incubated for 10 minutes at 37° C. to prepare a solution as a blank.

(2) The amount of ammonia generated by the reaction in the solution obtained in (1) is measured by using Ammonia-test Wako (manufactured by Wako Pure Chemical Industries, Ltd.). The ammonia concentration in the reaction solution is determined using a calibration curve indicating a relation between the ammonia concentration and the variation of absorbance (at 630 nm) prepared using an ammonia standard solution (ammonium chloride).

(3) The activity of the protein deamidating enzyme, where the amount of enzyme required to produce 1 μmol of ammonia per 1 min is defined as 1 unit, is calculated by the following formula:

$$\text{Enzymatic activity (u/mL)} = \text{the ammonium concentration in the reaction solution (mg/L)} \times (1/17.03) \times (2.1/0.1) \times (1/10) \times Df$$

where:
17.03 is the the molecular weight of ammonia;
2.1 is the volume of the solution of the enzyme reaction system;
0.1 is the volume of the enzyme solution;
10 is the reaction time; and
$Df$ is the dilution rate of the enzyme solution.

Two methods are described for preparing the aqueous phase part of the coffee whitener of the present invention. The first method is a method in which the protein deamidating enzyme is allowed to act after the milk protein content of the solution containing milk protein is prepared by dissolving so as to be 0.05 to 5% by weight, preferably 0.15 to 3% by weight (a pre-incubation method). The other method is a method in which the milk protein is deamidated with a protein deamidating enzyme in advance and is re-dissolved in the aqueous phase (an addition method of deamidated milk protein). That is, it is a method such that a solution containing a milk protein is treated with a protein deamidating enzyme to prepare a deamidated milk protein, then with using the solution itself or one dried and powdered thereof, the solution is prepared so as to be 0.05 to 5% by weight, preferably 0.15 to 3% by weight of the deamidated protein content. In either method, the enzyme may be deactivated suitably by heating at 75° C. or above.

Subsequently, the method in which the protein deamidating enzyme is added to the milk protein and is reacted therein is explained. In the present invention, it is important to perform the enzymatic reaction such that the deamidation rate of the milk protein is to be 70% or above, and the enzymatic reaction conditions (such as an amount of the enzyme, reaction time, temperature, pH of the reaction solution, etc.) for achieving such a state may be suitably set, in order that the deamidation rate of the milk protein in the milk raw material mixed-solution is to be within a proper range. The higher the deamidation rate is, the more preferable, and in the case where it is less than 70% a problem arises that a small diameter of an emulsion particle is not obtained and a sufficient storage stability is not acquired. For example, in a case where the amount of enzyme is low, although the reaction time may be elongated, the general addition amount of the protein deamidating enzyme is preferably 0.01 to 100 units, and more preferably 0.1 to 25 units per 1 g of the milk protein (dried weight). A preferable reaction temperature is 5 to 80° C., and more preferably 20 to 60° C. Preferably, the pH of the reaction solution is 2 to 10, and more preferably 4 to 8. Preferably, the reaction time is from 10 seconds to 48 hours, and more preferably from 10 minutes to 24 hours.

The deamidation rate used in the present invention shows to what degree glutamine residues in the milk proteins of the milk protein solution which is the aqueous phase were deamidated with the protein deamidating enzyme. The state where all glutamines in proteins in the milk raw material mixed-solution are deamidated is 100%. In a case where 15 units of the enzyme is added to 1 g of the milk protein and the resulting mixture is subjected to reaction at 55° C. for an hour, the deamidation reaction reaches saturation. Thereby, a maximum reaction amount (an amount of ammonia) which shows 100% of the deamidation rate can be obtained. That is, the deamidation rate is obtained based on the following formula.

The deamidation rate (%)=[the amount of ammonia in the milk raw material mixed-solution in case of reacting the protein deamidating enzyme into the milk raw material mixed-solution]÷[the amount of ammonia in the milk raw material mixed-solution in case of reacting for an hour at 55° C. by adding the same enzyme (15 units/1 g milk protein) into the same milk raw material mixed-solution]×100

The amount of ammonia generated by the deamidation reaction can be measured by commercially available ammonia measuring kit. For example, the enzymatic reaction is stopped by adding to the milk raw material mixed-solution (as for the pre-incubation method) or the milk protein solution (as for the addition method of deamidated milk protein) 12% TCA of the same quantity as the solution, and the amount of ammonia in the supernatant obtained by centrifugation (12,000 rpm, 5° C., 5 minutes) is measured using F-kit (Roche). In detail, 10 μl of the supernatant and 190 μl of 0.1 M triethanolamine buffer (pH 8.0) are added to 100 μl of liquid reagent II (a component of the F-kit) and settled for 5 minutes at room temperature. After that an absorbance at 340 nm is measured using 100 μl of the resultant solution. 1.0 μl of reagent III (a component of the F-kit, glutamate dehydrogenase) is added to the remaining 200 μl of the solution and settled for 20 minutes at room temperature and then the absorbance at 340 nm is measured using the 200 μl of the solution. The ammonia concentration in the supernatant is determined using a calibration curve indicating the relation between the ammonia concentration and the variation of absorbance (at 340 nm) prepared using an ammonia standard solution attached to the F-kit, and thereby the amount of ammonia in the milk raw material mixed-solution or the milk protein solution is determined. In addition, in a case where the measurement is out of the range of standard curve, the solution for measurement is appropriately diluted with water, and then measured.

Although it is characterized in that the composition of the coffee whitener has 10 to 40% by weight of vegetable oil as the oil phase and 60 to 90% by weight of the deamidated milk protein solution as the aqueous phase and the synthetic emulsifier is not formulated, salts (an phosphate, citric salt, etc.) and/or saccharide for the purpose of adjustment of sweet taste or viscosity may also be appropriately added. As a saccharide, starch syrup, powdered-starch, sucrose, maltose, sorbitol, maltitol, erythritol, trehalose etc. are listed, and these are suitably combined and formulated if necessary, for example.

As the synthetic emulsifier which is not used for the coffee whitener of the present invention, monoglyceride, glycerine fatty acid ester, organic acid monoglyceride, organic acid glycerine fatty acid ester, propylene glycol fatty acid ester, sucrose fatty acid ester, sorbitan fatty acid ester, polysorbate, poly glycerine fatty acid ester, etc. are listed.

The coffee whitener of the present invention can be processed by mixing the above-mentioned oil phase of 10 to 40 parts by weight and aqueous phase of 60 to 90 parts by weight, and homogenizing in accordance with an ordinary method. For example, while preparing an oil phase composition comprising vegetable oil, separately preparing an aqueous phase composition comprising the deamidated milk protein solution, and both compositions are heated to a suitable temperature and preparatorily homogenized with mixing and stirring, and then a coffee whitener is obtained through usual homogenizing process, sterilizing process, aseptic homogenizing process, cooling process, and aging process. The homomixer or the homogenizer used for homogenization is not limited in particular to this apparatus, any apparatus having an emulsifying ability can be used.

As a beverage processed using the coffee whitener of the present invention, coffee, tea etc. are listed, and a canned product thereof and a bottled product of PET thereof are also encompassed.

Other features of the invention will become apparent in the course of the following descriptions of exemplary embodiments which are given for illustration of the invention and are not intended to be limiting thereof.

EXAMPLES

Example 1

Under fully deamidated conditions, i.e., a protein deamidating enzyme was added by 15 U per 1 g of proteins in 10% (w/w) solution of low-heat defatted milk powder (Yotsuba Nyugyo, protein 35.6%), and then subjected to reaction at 55° C. for 60 minutes. A protein glutaminase (manufactured by Amano Enzyme Inc., 500 U/g, derived from genera *Chryseobacterium;* hereinafter may be abbreviated as PG) was used as a protein deamidating enzyme. After that, the solution was heated until reaching 80° C. in a boiling bath so that the enzyme was deactivated, and then the solution was cooled. Next, after freezing at −80° C. for powdering, it was subjected to freeze-drying, and a PG-treated defatted milk powder whose deamidation rate is 100% was prepared. Similarly, the PG was added by 1.5 U, 4 U, and 15 U respectively per 1 g of protein and subjected to reaction at 55° C. for 60 minutes, after that the enzyme was deactivated by heating, and then the solution was cooled. Next, after freezing at −80° C. for powdering, it was subjected to freeze-drying, and the defatted milk powder treated with protein deamidating enzyme whose deamidation rate is 27.5%, 70.4% and 100%, respectively, were prepared.

Thus-prepared three kinds of defatted milk powder having different deamidation rates were dissolved in water so that the milk protein content is 0.15% by weight (aqueous phase), respectively. This was mixed with corn oil (oil phase), wherein the mixing ratio of the aqueous phase versus the oil phase was 80:20, and ultrasonic emulsification (Handy Sonic; TOMY SEIKO CO., LTD.) was performed at output 9 for 30 seconds. The particle size in diameter of the obtained oil-in-water (o/w) emulsion was measured with a particle-size-distribution meter (Microtrac; NIKKISO CO., LTD.). The results ate shown in Table 1, in which "PG addition amount (U/gp) in Table 1 means "PG addition amount (U/gram of milk protein)".

TABLE 1

|  | PG addition amount (U/gp) | Deamidation rate (%) | Mean particle size in diameter (μm) | after one-week ambient temperature storage after-heating |
|---|---|---|---|---|
| Control product | 0 | 0.0 | 9.01 | Poor |
| Compared product | 1.5 | 27.5 | 7.49 | Poor |
| Invention product | 4 | 70.8 | 4.68 | Good |
| Invention product | 15 | 100.0 | 4.05 | Good |

As for the non-addition of the protein deamidating enzyme (control product) and the protein deamidating enzyme-treated (27.5% deamidation rate) (compared product) with 1.5 U/gp (U/gp means U/gram of milk protein hereinafter), the mean particle size in diameter of the emulsions were 9.0 μm and 7.5 μm, respectively, and the state after one-week normal temperature storage after-heating was poor, and a separation between the aqueous phase and the oil phase occurred. On the other hand, as for the protein deamidating enzyme-treated (deamidation rate is 70.4% and 100%, respectively) (the present invention products) with 4 U/gp and 15 U/gp, the mean particle sizes in diameter of the emulsions were 4.7 μm, 4.1 μm, respectively, and small compared to the control product and the compared product, and the state after one-week normal temperature storage after-heating was good without separation. Thus, it was shown that an emulsion in which emulsifying capacity and emulsification stability are good at the deamidation rate of 70% or above.

Example 2

Coffee whiteners comprising the oil-in-water emulsion having compositions shown in Table 2 were prepared. Solutions which contain sodium caseinate of 3%, 1.5%, and 0.5% were treated with protein deamidating enzyme of 4 U/gp and 10 U/gp, then the solutions were heated until reaching 80° C. so that the enzyme was deactivated. Thus-prepared the aqueous phase of 560 parts by weight and corn oil (oil phase) of 140 parts by weight were mixed, and this mixture was preliminarily emulsified at 55° C. The preliminary emulsification was performed with TK homomixer (made by Tokushu-kika kogyo) and the treating condition was 5 minutes at 5000 rpm. After preliminary emulsification, the solutions were homogenized at 300 bar (first pressure 60 bar, second pressure 240 bar) by using High-pressure homogenizer (SMT CO., LTD.) The mean particle size in diameter of the obtained emulsion was measured and the remaining emulsion was moved to the transparent container as storage tests (samples) at 5° C. and 55° C. The storage stability was evaluated from the measurement of the mean particle size and an appearance observation after storage for 15 days. Products which were treated with the same process were prepared, except for not adding enzyme in the solutions which contain sodium caseinate of 0.5%, 1.5% and 3%, as control products. Moreover, as compared products, the aqueous phase was prepared by adding 0.1%, 0.5%, and 1.0% sucrose glycerin ester (P-1670; made by Mitsubishikagaku Foods corporation) as a synthetic emulsifier into 1.5% sodium caseinate solution, and the same process as the above was performed. The results of the above tests are shown in Table 3.

TABLE 2

|  | 1 Control product | 2 Control product | 3 Control product | 4 Compared product | 5 Compared product | 6 Compared product |
|---|---|---|---|---|---|---|
| Casein Na (%) | 3 | 1.5 | 0.5 | 1.5 | 1.5 | 1.5 |
| Emulsifier (%) | 0 | 0 | 0 | 1 | 0.5 | 0.1 |
| PG (%) | 0 | 0 | 0 | 0 | 0 | 0 |
| Water (%) | 97 | 98.5 | 99.5 | 98.5 | 98.5 | 98.5 |
| Total | 100 | 100 | 100 | 101 | 100.5 | 100.1 |
| PG (U) | 0 | 0 | 0 | 0 | 0 | 0 |
| PG (U/g of Casein Na) | 0 | 0 | 0 | 0 | 0 | 0 |

|  | 7 Invention product | 8 Invention product | 9 Invention product | 10 Invention product | 11 Invention product | 12 Invention product |
|---|---|---|---|---|---|---|
| Casein Na (%) | 3 | 3 | 1.5 | 1.5 | 0.5 | 0.5 |
| Emulsifier (%) | 0 | 0 | 0 | 0 | 0 | 0 |
| PG (%) | 0.024 | 0.06 | 0.012 | 0.03 | 0.004 | 0.01 |
| Water (%) | 96.976 | 96.94 | 98.488 | 98.47 | 99.496 | 99.49 |
| Total | 100 | 100 | 100 | 100 | 100 | 100 |
| PG (U) | 12 | 30 | 6 | 15 | 2 | 5 |
| PG (U/g of Casein Na) | 4 | 10 | 4 | 10 | 4 | 10 |

TABLE 3

| | | Mean particle size in diameter of emulsion (μm) | | | | | |
|---|---|---|---|---|---|---|---|
| Storage temperature (°C.) | Storage days (days) | 1 control product | 2 control product | 3 control product | 4 compared product | 5 compared product | 6 compared product |
| — | 0 | 0.648 | 0.677 | 1.244 | 0.485 | 1.513 | 0.747 |
| 5 | 15 | 3.919 | 2.151 | 2.330 | 0.455 | 5.339 | 4.054 |

TABLE 3-continued

| Storage temperature (°C) | Storage days (days) | | | | | |
|---|---|---|---|---|---|---|
| 55 | 15 | 20.193 | 5.465 | 10.106 | 0.476 | 1.537 | 1.601 |
| Total evaluation of storage stability | | X | X | X | ○ | Δ | X |

| | | Mean particle size of emulsion (μm) | | | | | |
|---|---|---|---|---|---|---|---|
| Storage temperature (°C) | Storage days (days) | 7 Invention product | 8 Invention product | 9 Invention product | 10 Invention product | 11 Invention product | 12 Invention product |
| — | 0 | 0.560 | 0.568 | 0.565 | 0.594 | 0.816 | 0.619 |
| 5 | 15 | 0.467 | 0.566 | 0.504 | 0.830 | 2.044 | 3.938 |
| 55 | 15 | 0.498 | 0.564 | 1.022 | 0.603 | 5.152 | 3.395 |
| Total evaluation of storage stability | | ○ | ○ | Δ | ○ | Δ | Δ |

In the control products 1-3, the mean particle size in diameter of the emulsion increased as the sodium caseinate content decreased. Moreover, irrespective of the sodium caseinate content, the change in the mean particle size in diameter under storage was large and the storage stability was low. In compared products 4-6, there was a tendency that the mean particle size in diameter of the emulsion increased and the storage stability decreased as the synthetic emulsifier content decreased. Accordingly, it is recognized that sodium caseinate and an emulsifier are necessary ingredients for producing a fine and stable emulsion. On the other hand, the mean particle size in diameter of the emulsion of samples (invention products 7-12) in which sodium caseinate, instead of the synthetic emulsifier (P-1670), was treated with the protein deamidating enzyme of 4 U/gp and 10 U/gp was all small compared to the same conditions of control products 1-3. Moreover, in the invention products 7-10 having the sodium caseinate content of 3% and 1.5%, the change in the particle size was suppressed and the stability was improved even in storage samples at 5° C. and 55° C. compared with the control products. Especially, as for the samples (invention products 7 and 8) in which 3% sodium caseinate was treated with the protein deamidating enzyme of 4 U/gp and 10 U/gp, its result is equal to the result of the sample with 1% addition of the synthetic emulsifier (P-1670), and this result can be said to be a result which shows that the sodium caseinate treated with the protein deamidating enzyme can be a substituted for the synthetic emulsifier (P-1670).

Next, the coffee test was performed for the control products 1-3 and the invention products 7-12. Hot water at 80° C. was poured into commercial available instant coffee, and a coffee solution of 1.5% by weight was produced. To 45 g of this coffee solution, 1.5 g of the coffee whitener sample was added and stirred well. The result of having detected the existence of agglomerates (feathering) is shown in Table 4. While many agglomerates were found with the increase in the sodium caseinate content in the control products, agglomerates were hardly found in the invention products 7-12.

TABLE 4

| 1 Control product | 2 Control product | 3 Control product | 7 Invention product | 8 Invention product | 9 Invention product | 10 Invention product | 11 Invention product | 12 Invention product |
|---|---|---|---|---|---|---|---|---|
| x | Δ | ○ | ○ | ○ | ○ | ○ | ○ | ○ |

○: almost no agglomerates found.
Δ: agglomerates found but a little.
x: agglomerates found.

Example 3

Coffee whiteners which comprise oil-in-water emulsions having compositions shown in Table 5 were prepared. The defatted milk powder and the PG which are described in Example 1 were used. The solutions which contain defatted milk powder of 1.5%, 4.5%, and 9% were treated with the protein deamidating enzyme of 10 U/gp, then the solutions were heated until reaching 80° C. so that the enzyme was deactivated (this is termed an "aqueous phase"). Similar to the above, the aqueous phase and corn oil (oil phase) were mixed, and this mixture was preliminarily emulsified at 55 C, followed by treatment with the high-pressure homogenizer. The mean particle size in diameter of the obtained emulsion was measured and the remaining emulsion was moved to the transparent container for storage tests at 5° C. and 55° C. The storage stability was evaluated from the measurement of the mean particle size in diameter and an appearance observation after storage for 15 days (the invention products 16, 17, and 18). Products which were treated with the same process were prepared except for not adding enzyme in the solutions which contain defatted milk powder 1.5%, 4.5%, and 9%, as control products (comparative examples 13, 14 and 15). The results are shown in Table 6.

TABLE 5

|  | 13 Compared example | 14 Compared example | 15 Compared example | 16 Invention product | 17 Invention product | 18 Invention product |
|---|---|---|---|---|---|---|
| Defatted milk powder (%) | 9 | 4.5 | 1.5 | 9 | 4.5 | 1.5 |
| Emulsifier (%) | 0 | 0 | 0 | 0 | 0 | 0 |
| PG (%) | 0 | 0 | 0 | 0.06 | 0.03 | 0.01 |
| water | 91 | 95.5 | 98.5 | 90.94 | 95.47 | 98.49 |
| total | 100 | 100 | 100 | 100 | 100 | 100 |
| PG (U) | 0 | 0 | 0 | 32 | 16 | 5 |
| PG (U/g) | 0 | 0 | 0 | 10 | 10 | 10 |

TABLE 6

| | | Mean particle size of emulsion (µm) | | | | | |
|---|---|---|---|---|---|---|---|
| Storage temperature (°C.) | Storage days (days) | 13 compared product | 14 compared product | 15 compared product | 16 Invention product | 17 Invention product | 18 Invention product |
| — | 0 | 0.648 | 0.677 | 1.244 | 0.540 | 0.590 | 1.780 |
| 5 | 15 | 0.800 | 36.900 | 48.100 | 0.549 | 0.599 | 1.140 |
| 55 | 15 | 20.193 | Unmeasurable | Unmeasurable | 0.476 | 1.537 | 1.601 |
| Total evaluation of storage stability | | X | X | X | ○ | Δ | Δ |

As for all control (compared) products, the mean particle sizes of the emulsions under storage at 5° C. and 55° C. increased remarkably and had remarkable agglomeration-separation, compared to immediately after the preparation. Especially, for the samples under storage at 55° C., it was difficult to measure the mean particle size in diameter. On the other hand, as for the invention products 16-17, the mean particle sizes in diameter of the emulsions were maintained with a small size(s), compared to the samples having the same conditions as the control products. Especially for the invention product 16, it is recognized to show a good stability that the mean particle size in diameter of the emulsion did not change for 15 days at any storage temperature of 5° C. and 55° C. This result is equal to the result in which the synthetic emulsifier (P-1670) shown as the compared product 4 in Table 3 was used, and it can be said to be a result which shows that the defatted milk powder treated with the protein deamidating enzyme can be substituted for the synthetic emulsifier.

Using the compared product 13 and the invention product 16 shown in Table 5, the dispersibility to the coffee beverage was evaluated on each sample of the coffee whitener, one without adjusting pH (pH 6.7) and others with adjusting pH by sodium bicarbonate (pH 7.1 to 7.8). Each sample of the coffee whitener was added to a coffee solution of 1.5% by weight (the preparation method is as described in Example 2 of the present application), and a state of agglomeration was observed. As for the invention products, generation of the agglomeration was suppressed at any pH value, compared to the control products, and especially agglomeration was hardly found for the products with adjusting pH to 7 or above. According to this result, a high effect of the treatment with the protein deamidating enzyme by adjusting pH is expected.

It should be noted that changes and modifications of the modes or examples may be done within the entire disclosure (inclusive of the claims) of the present invention and on the basis of the basic technical concept thereof. Also, it should be noted that a variety of combinations or selections of various elements as disclosed may be made within the scope of the claims of the present invention. That is, it should be noted that the present invention also includes various changes and modifications which can be made by a person skilled in the art on the basis of the entire disclosure (inclusive of the claims) and technical concept.

INDUSTRIAL APPLICABILITY

According to the present invention, since a coffee whitener which is excellent in not only the storage stability but also the dispersibility, without using a synthetic emulsifier can be obtained, the present invention is very useful for the food industries.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A coffee whitener, in which:
(a) said coffee whitener is an oil-in-water emulsion, comprising 60 to 90% by weight, based on the total weight of said coffee whitener, of an aqueous phase and 10 to 40% by weight, based on the total weight of said coffee whitener, of an oil phase;
(b) said aqueous phase is a casein-containing milk protein solution which comprises a casein-containing milk protein in an amount of 0.05 to 5% by weight, based on the total weight of said aqueous phase;

(c) said milk protein has been subjected to a treatment with a protein deamidating enzyme;
(d) said milk protein has a degree of a deamidation rate of 70% or above;
(e) said oil phase comprises at least one vegetable oil; and
(f) said coffee whitener does not contain any synthetic emulsifier as an active ingredient.

2. A coffee whitener according to claim 1, which has a pH of 6.7 to 7.8.

3. A coffee whitener according to claim 1, wherein said casein-containing milk protein solution is a solution comprising 0.05 to 5% by weight, based on the total weight of said solution, of sodium caseinate or a solution comprising 0.1 to 15% by weight, based on the total weight of said solution, of defatted milk powder.

4. A coffee whitener according to claim 1, wherein said protein deamidating enzyme is an enzyme derived from genera *Chryseobacterium*.

5. A method for producing a coffee whitener in which no synthetic emulsifier is used, comprising:
(A) preparing a casein-containing milk protein solution which comprises a casein-containing milk protein in an amount of 0.05 to 5% by weight, based on the total weight of said solution;
(B) adding a protein deamidating enzyme to said casein-containing milk protein solution and allowing said protein deamidating enzyme to act on said casein-containing milk protein, to obtain a deamidated milk protein solution which comprises a deamidated milk protein which has a deamidation rate of 70% or above; and
(C) mixing and homogenizing 60 to 90 parts by weight of an aqueous phase which comprising said deamidated milk protein solution with 10-40 parts by weight of an oil phase which comprises at least one vegetable oil to obtain an oil-in-water emulsion.

6. A method according to claim 5, wherein said casein-containing milk protein solution is a solution comprising 0.05 to 5% by weight, based on the total weight of said solution, of sodium caseinate or a solution comprising 0.1 to 15% by weight, based on the total weight of said solution, of defatted milk powder.

7. A method according to claim 5, wherein said protein deamidating enzyme is added to said casein-containing milk protein solution in an amount of 0.1 to 100 units per 1 g of milk protein.

8. A method according to claim 5, wherein said protein deamidating enzyme is an enzyme derived from genera *Chryseobacterium*.

9. A method for producing a coffee whitener in which no synthetic emulsifier is usaed, comprising:
(A) allowing a protein deamidating enzyme to act on a casein-containing milk protein to obtain a deamidated milk protein which has a deamidation rate of 70% or above;
(B) dissolving said deamidated milk protein to obtain a deamidated milk protein solution which comprises said deamidated milk protein in an amount of 0.05 to 5% by weight, based on the total weight of said solution; and
(C) mixing and homogenizing 60-90 parts by weight of an aqueous phase which comprises said deamidated milk protein solution with 10-40 parts by weight of an oil phase which comprises at least one vegetable oil to obtain an oil-in-water emulsion.

10. A method according to claim 9, wherein said protein deamidating enzyme is added to said milk protein in an amount of 0.1 to 100 units per 1 g of said milk protein.

11. A method according to claim 9, wherein said protein deamidating enzyme is an enzyme derived from genera *Chryseobacterium*.

12. A method for producing a beverage, comprising adding a coffee whitener according to claim 1 to a beverage.

13. A method for producing a beverage, comprising adding a coffee whitener which is produced by a method according to claim 5 to a beverage.

14. A method for producing a beverage, comprising adding a coffee whitener which is produced by a method according to claim 9 to a beverage.

* * * * *